(12) United States Patent
Koch et al.

(10) Patent No.: US 12,139,736 B2
(45) Date of Patent: Nov. 12, 2024

(54) BACTERIAL STRAIN FOR RELEASING A RECOMBINANT PROTEIN IN A FERMENTATION METHOD

(71) Applicant: WACKER CHEMIE AG, Munich (DE)

(72) Inventors: Johanna Koch, Munich (DE); Markus Brunner, Mering (DE)

(73) Assignee: WACKER CHEMIE AG, Munich (DE)

(*) Notice: Subject to any disclaimer, the term of this patent is extended or adjusted under 35 U.S.C. 154(b) by 932 days.

(21) Appl. No.: 17/258,252

(22) PCT Filed: Jul. 6, 2018

(86) PCT No.: PCT/EP2018/068418
§ 371 (c)(1),
(2) Date: Jan. 6, 2021

(87) PCT Pub. No.: WO2020/007493
PCT Pub. Date: Jan. 9, 2020

(65) Prior Publication Data
US 2021/0269843 A1  Sep. 2, 2021

(51) Int. Cl.
*C12P 21/02* (2006.01)
*C07K 1/14* (2006.01)
*C07K 14/775* (2006.01)
*C12N 15/70* (2006.01)
*C12R 1/19* (2006.01)

(52) U.S. Cl.
CPC .............. *C12P 21/02* (2013.01); *C07K 1/14* (2013.01); *C07K 14/775* (2013.01); *C12N 15/70* (2013.01); *C12R 2001/19* (2021.05)

(58) Field of Classification Search
CPC ......... C12P 21/02; C07K 1/14; C07K 14/775; C07K 14/245; C12N 15/70; C12R 2001/19
See application file for complete search history.

(56) References Cited

U.S. PATENT DOCUMENTS

| 8,053,211 B2 | 11/2011 | Dassler et al. |
| 2008/0076157 A1 | 3/2008 | Leonhartsberger et al. |
| 2008/0076158 A1 | 3/2008 | Dassler et al. |
| 2008/0254511 A1 | 10/2008 | Dassler et al. |

FOREIGN PATENT DOCUMENTS

| CN | 102827860 B | 6/2014 | |
| CN | 102827904 B | 6/2014 | |
| EP | 2204441 B1 | 7/2011 | |
| EP | 1905839 B2 | 7/2019 | |
| WO | WO-2010008764 A1 * | 1/2010 | ............. C12N 15/78 |
| WO | WO-2016005931 A1 * | 1/2016 | ............. A01H 6/342 |
| WO | WO-2017097383 A1 * | 6/2017 | ............. C07K 14/195 |

OTHER PUBLICATIONS

Alan Bernstein et al., "Pleiotropic Properties and Genetic Organization of the toIA, B Locus of *Escherichia coli* K-12", Journal Of Bacteriology, Oct. 1972, vol. 12, No. 1, pp. 74-83, American Society for Microbiology, U.S.A.

Usama Beshay et al., "Increasing the secretion ability of the kil gene for recombinant proteins in *Escherichia coli* by using a strong stationary-phase promoter", Biotechnology Letters, 2007, vol. 29, pp. 1893-1901, Springer Science+Business Media, Germany.

Michele Bruschi et al., "Production of the short peptide surfactant DAMP4 from glucose or sucrose in high cell density cultures of *Escherichia coli* BL21(DE3)", Microbial Cell Factories, 2014, vol. 13, pp. 1-9, Springer Nature, Germany.

Eric Cascales et al., "Pal Lipoprotein of *Escherichia coli* Plays a Major Role in Outer Membrane Integrity", Journal Of Bacteriology, Feb. 2002, vol. 184, No. 3, pp. 754-759, American Society for Microbiology, U.S.A.

Robert Chen et al., "Nucleotide sequence of the gene for the peptidoglycan-associated lipoprotein of *Escherichia coli* K12", European Journal of Biochemistry, Feb. 1987, vol. 163, pp. 73-77, John Wiley and Sons, UK.

Zhao-Yuan Chen et al., "Construction of leaky strains and extracellular production of exogenous proteins in recombinant *Escherichia coli*", Microbial Biotechnology, 2014, vol. 7, pp. 360-370, John Wiley & Sons Ltd and Society for Applied Microbiology, UK.

J.H. Choi et al., "Secretory and extracellular production of recombinant proteins using *Escherichia coli*", Journal of Applied Microbiology and Biotechnology, 2004, vol. 64, pp. 625-635, Springer Science+Business Media, Germany.

Thierry Clavel et al., "ToIB protein of *Escherichia coli* K-12 interacts with the outer membrane peptidoglycan-associated proteins Pal, Lpp and OmpA", Molecular Microbiology, 1998, vol. 29, No. 1, pp. 359-367, Wiley Online Library.

Alexandra Gennaris et al., "Repairing oxidized proteins in the bacterial envelope using respiratory chain electrons", Nature Research Letter, Dec. 2015, vol. 528, pp. 409-426, and Research Supplementary Information, (Supplementary Tables), Macmillan Publishers, UK.

(Continued)

*Primary Examiner* — Soren Harward
*Assistant Examiner* — Naghmeh Nina Moazzami
(74) *Attorney, Agent, or Firm* — BROOKS KUSHMAN P.C.

(57) ABSTRACT

A bacterial strain suitable for expressing recombinant proteins contains an open reading frame which codes for a recombinant protein, under control of a functional promoter. The bacterial strain contains an open reading frame which codes for a muted peptidologycan-associated lipoprotein (PAL protein), under control of a functional promoter, wherein the PAL protein is muted such that it contains no membrane anchor for the outer cell membrane of the bacterial strain. A plasmid codes for a recombinant protein. Fermentative production of recombinant protein is facilitated by using the bacterial strain, with increased product yields in the culture residue without leading to a substantial die-off of the bacterial cells.

13 Claims, 5 Drawing Sheets
Specification includes a Sequence Listing.

(56) References Cited

OTHER PUBLICATIONS

J.K. Dhillon et al., "Bacterial surface display of an anti-pollutant antibody fragment", Letters in Applied Microbiology, 1999, vol. 28, pp. 350-354, Society for Applied Microbiology, London, UK.

Patrick Fuchs et al., "Targeting recombinant antibodies to the surface of *Escherichia coli*: Fusion to a peptidoglycan associated lipoprotein", BioTechnology, 1991, vol. 9, pp. 1369-1372, Nature Publishing Group, Germany.

Chou-Zen Giam et al., "Prolipoprotein modification and processing in *Escherichia coli*. A unique secondary structure in prolipoprotein signal sequence for the recognition by glyceryl transferase", European Journal of Biochemistry, 1984, vol. 141, pp. 331-337, Wiley, UK.

Renata Godlewska et al., "Peptidoglycan-associated lipoprotein(Pal)of Gram-negative bacteria: function, structure, role in pathogenesis and potential application in immunoprophylaxis", FEMS Microbiology Letters, 2009, vol. 298, pp. 1-11, Federation of European Microbiological Societies.

Shigeru Hayashi et al., "Lipoproteins in Bacteria", Journal of Bioenergetics and Biomembranes, 1990, vol. 22, No. 3, Springer, Germany.

Ingo Knabben et al., "High cell-density processes in batch mode of a genetically engineered *Escherichia coli* strain with minimized overflow metabolism using a pressurized bioreactor", Journal of Biotechnology, 2010, vol. 150, pp. 73-79, Elsevier B.V., NL.

Anna Konovalova et al., "Outer membrane lipoprotein biogenesis: Lol is not the end", Philosophical Transactions B, 2015, vol. 370: 20150030, UK.

Jean-Claude Lazzaroni et al., "Genetic and Biochemical Characterization of Periplasmic-Leaky Mutants of *Escherichia coli* K-12", Journal of Bacteriology, Mar. 1981, vol. 145, No. 3, pp. 1351-1358, American Society for Microbiology, U.S.A.

Jean-Claude Lazzaroni et al., "The exeC gene of *Escherichia coli* K-12 required for cell envelope integrity encodes the peptidoglycan-associated lipoprotein (PAL)", Molecular Microbiology, 1991, vol. 6, No. 6, pp. 735-742, Wiley Online Library.

Sharyn K. Levengood-Freyermuth et al., "Role of the Carboxyl-Terminal Domain of TolA in Protein Import and Integrity of the Outer Membrane", Journal of Bacteriology, Jan. 1993, vol. 175, No. 1, pp. 222-228, American Society for Microbiology, U.S.A.

Takeshi Mizunoa, "A Novel Peptidoglycan-Associated Lipoprotein Found in the Cell Envelope of Pseudomonas aeruginosa and *Escherichia coli*", Journal of Biochemistry, 1979, vol. 86, No. 4, pp. 991-1000, Oxford University Press, UK.

Johan Robbens et al., "Production of Soluble and Active Recombinant Murine Interleukin-2 in *Escherichia coli*: High Level Expression, Kil-induced Release, and Purification", Protein Expression and Purification, 1995, vol. 6, pp. 481-486, Elsevier, NL.

Atefeh Shokri et al., "Characterisation of the *Escherichia coli* membrane structure and function during fedbatch cultivation", Microbial Cell Factories, 2004, vol. 3, No. 9, BioMed Central Ltd.

Benjamin Sommer et al., "Efficient production of extracellular proteins with *Escherichia coli* by means of optimized coexpression of bacteriocin release proteins", Journal of Biotechnology, 2010, vol. 145, pp. 350-358, Elsevier, NL.

Eugene W.-M. Wan et al., "TolAIII Co-overexpression Facilitates the Recovery of Periplasmic Recombinant Proteins Into the Growth Medium of *Escherichia coli*", Protein Expression and Purification, 1998, vol. 14, pp. 13-22, Article No. PT980941, Elsevier, NL.

Wolfram R. Zueckert, "Secretion of Bacterial Lipoproteins: Through the Cytoplasmic Membrane, the Periplasm and Beyond", Biochimica et Biophysica Acta 1843, 2014, pp. 1509-1516, Elsevier, NL.

* cited by examiner

SEQUENCE LISTING

<160> NUMBER OF SEQ ID NOS: 7

<210> SEQ ID NO 1
<211> LENGTH: 816
<212> TYPE: DNA
<213> ORGANISM: Artificial Sequence
<220> FEATURE:
<223> OTHER INFORMATION: DNS-Fragment xI

```
<220> FEATURE:
<221> NAME/KEY: misc_feature
<222> LOCATION: (1)..(816)

<400> SEQUENCE: 1
caattcgcgc gcgtaacaaa agtgtctata atcacggcag aaaagtccac attgattatt      60
tgcacggcgt cacactttgc tatgccatag cattttttatc cataagatta gcggatccta    120
cctgacgctt tttatcgcaa ctctctactg tttctccata cccgtttttt tgggctagaa    180
ataattttgt ttaagaattc taaggaggaa attatatgca actgaacaaa gtgctgaaag    240
ggctgatgat tgctctgcct gttatggcaa ttgcggcagc cagcaatgac ggcagcgaag    300
gcatgctggg tgccggcact ggtatggatg cgaacggcgg caacggcaac atgtcttccg    360
aagagcaggc tcgtctgcaa atgcaacagc tgcagcagaa caacatcgtt tacttcgatc    420
tggacaagta cgatatccgt tctgacttcg ctcaaatgct ggatgcacat gcaaacttcc    480
tgcgtagcaa cccgtcttac aaagtcaccg tagaaggtca cgcggacgaa cgtggtactc    540
cggaatacaa catctccctg ggtgaacgtc gtgcgaacgc cgttaagatg tacctgcagg    600
gtaaaggcgt ttctgcagac cagatctcca tcgtttctta cggtaaagaa aaacctgcag    660
tactgggtca tgacgaagcg gcatactcca aaaaccgtcg tgcggtactg gtttactaag    720
aattgcaagc tggccgacgc gtcccacagc cgccagttcc gctggcggca ttttaacttt    780
ctttaatgaa gccggaaaaa tcccgcgcgc gaaggc                              816

<210> SEQ ID NO 2
<211> LENGTH: 771
<212> TYPE: DNA
<213> ORGANISM: Artificial Sequence
<220> FEATURE:
<223> OTHER INFORMATION: DNS-Fragment xII
<220> FEATURE:
<221> NAME/KEY: misc_feature
<222> LOCATION: (1)..(771)

<400> SEQUENCE: 2
caattcgcgc gcgtaacaaa agtgtctata atcacggcag aaaagtccac attgattatt      60
tgcacggcgt cacactttgc tatgccatag cattttttatc cataagatta gcggatccta    120
cctgacgctt tttatcgcaa ctctctactg tttctccata cccgtttttt tgggctagaa    180
ataattttgt ttaagaattc taaggaggaa attatatgaa aaagacagct atcgcgattg    240
cagtggcact ggctggtttc gctaccgtag cgcaggctgc cgcagaggca gatgatattt    300
tcggtgagct aagctctggt aagaatgcac cgaaaacggg gggaggggcg aaagggaaca    360
atgcttcgcc tgccgggagt ggtaatacta aaaacaatgg cgcatcaggg gccgatatca    420
ataactatgc cgggcagatt aaatctgcta tcgaaagtaa gttctatgac gcatcgtcct    480
atgcaggcaa aacctgtacg ctgcgcataa aactggcacc cgatggtatg ttactggata    540
tcaaacctga aggtggcgat cccgcacttt gtcaggctgc gttggcagca gctaaacttg    600
cgaagatccc gaaaccacca agccaggcag tatatgaagt gttcaaaaac gcaccattgg    660
acttcaaacc gtaagaattg caagctggcc gacgcgtccc acagccgcca gttccgctgg    720
cggcatttta actttcttta atgaagccgg aaaaatcccg cgcgcgaagg c              771

<210> SEQ ID NO 3
<211> LENGTH: 1599
<212> TYPE: DNA
<213> ORGANISM: Artificial Sequence
<220> FEATURE:
```

<223> OTHER INFORMATION: DNS-Fragment xIII
<220> FEATURE:
<221> NAME/KEY: misc_feature
<222> LOCATION: (1)..(1599)

<400> SEQUENCE: 3

```
acagaattct aaggaggaaa ttatatgaaa agaaaccgtt tttttaatac ctcggctgct    60
attgccattt cgattgcatt acagatcttt tttccgtccg cttccgcttt cgctcaggtt   120
cagctggtgc agagcggtgc cgaagttgtt aaaccgggtg caagcgttaa actgagctgt   180
aaagcaagcg gctatatttt taccagctat tatatgtatt gggtgaaaca ggcaccgggt   240
cagggtctgg aatggattgg tgaaattaat ccgagcaatg gcgataccaa ttttaatgaa   300
aaatttaaaa gcaaagccac cctgaccgtt gataaaagcg caagcaccgc atatatggaa   360
ctgagcagcc tgcgtagcga agataccgca gtttattatt gtacccgtag tgatggtcgc   420
aatgatatgg atagctgggg tcagggcacc ctggtcaccg ttagcagcgc aagcaccaaa   480
ggtccgagcg ttttccgct ggcaccgagc agcaaaagca ccagcggtgg caccgcagca   540
ctgggttgtc tggttaaaga ttatttccg gaaccggtta cagttagctg gaatagcggt   600
gcactgacca gtggtgttca tacctttccg gcagttctgc aaagcagcgg tctgtatagc   660
ctgagcagcg ttgttaccgt tccgagcagt agcctgggca cccagaccta tatttgtaat   720
gttaatcata aaccgagcaa caccaaagtg gataaaaaag ttgaaccgaa aagctgctaa   780
taaccatgga gaaaataaag tgaaacaaag cactattgca ctggcactct taccgttact   840
cttcaccect gttaccaaag ccgatattgt gctcacccag agtccggcaa ccctgagcgt   900
tagtccgggt gaacgtgcaa ccattagctg tcgtgcaagc cagcgtgtta gcagcagcac   960
ctatagctat atgcattggt atcagcagaa accgggtcag cctccgaaac tgctgattaa  1020
atatgcaagc aatctggaaa gcggtgttcc ggcacgtttt agcggtagcg gtagtggcac  1080
cgatttacc ctgaccatta gcagcgttga accggaagat tttgccacct attattgtca  1140
gcatagctgg gaaattcctc cgacctttgg tggtggcacc aaactcgaga ttaaacgtac  1200
cgttgcagca ccgagcgtgt ttatctttcc gcctagtgat gaacagctga aaagcggcac  1260
cgcaagcgtt gttgtctgc tgaataactt ttatccgcgt gaagcaaaag ttcagtggaa  1320
agttgataat gcactgcaaa gcggtaatag ccaagaaagc gttaccgaac aggatagcaa  1380
agatagcacc tatagcctgt caagcaccct gaccctgagc aaagcagatt atgaaaaaca  1440
caaagtgtat gcctgcgaag ttacccatca gggtctgagc agtccggtta caaaaagttt  1500
taatcgtggt gaatgtagct cttctgccca tcaccaccat caccattaat aagcttctag  1560
aagcttggct gttttggcgg atgagagaag attttcgac                         1599
```

<210> SEQ ID NO 4
<211> LENGTH: 173
<212> TYPE: PRT
<213> ORGANISM: Escherichia coli
<220> FEATURE:
<221> NAME/KEY: PEPTIDE
<222> LOCATION: (1)..(173)
<223> OTHER INFORMATION: Wildtyp-Pal-Protein

<400> SEQUENCE: 4

```
Met Gln Leu Asn Lys Val Leu Lys Gly Leu Met Ile Ala Leu Pro Val
1               5                   10                  15

Met Ala Ile Ala Ala Cys Ser Ser Asn Lys Asn Ala Ser Asn Asp Gly
            20                  25                  30
```

```
Ser Glu Gly Met Leu Gly Ala Gly Thr Gly Met Asp Ala Asn Gly Gly
             35                  40                  45

Asn Gly Asn Met Ser Ser Glu Glu Gln Ala Arg Leu Gln Met Gln Gln
 50                  55                  60

Leu Gln Gln Asn Asn Ile Val Tyr Phe Asp Leu Asp Lys Tyr Asp Ile
 65                  70                  75                  80

Arg Ser Asp Phe Ala Gln Met Leu Asp Ala His Ala Asn Phe Leu Arg
                 85                  90                  95

Ser Asn Pro Ser Tyr Lys Val Thr Val Glu Gly His Ala Asp Glu Arg
                100                 105                 110

Gly Thr Pro Glu Tyr Asn Ile Ser Leu Gly Glu Arg Arg Ala Asn Ala
                115                 120                 125

Val Lys Met Tyr Leu Gln Gly Lys Gly Val Ser Ala Asp Gln Ile Ser
                130                 135                 140

Ile Val Ser Tyr Gly Lys Glu Lys Pro Ala Val Leu Gly His Asp Glu
145                 150                 155                 160

Ala Ala Tyr Ser Lys Asn Arg Arg Ala Val Leu Val Tyr
                165                 170

<210> SEQ ID NO 5
<211> LENGTH: 167
<212> TYPE: PRT
<213> ORGANISM: Artificial Sequence
<220> FEATURE:
<223> OTHER INFORMATION: PalD22-27
<220> FEATURE:
<221> NAME/KEY: PEPTIDE
<222> LOCATION: (1)..(167)

<400> SEQUENCE: 5

Met Gln Leu Asn Lys Val Leu Lys Gly Leu Met Ile Ala Leu Pro Val
 1               5                  10                  15

Met Ala Ile Ala Ala Ala Ser Asn Asp Gly Ser Glu Gly Met Leu Gly
                 20                  25                  30

Ala Gly Thr Gly Met Asp Ala Asn Gly Gly Asn Gly Asn Met Ser Ser
                 35                  40                  45

Glu Glu Gln Ala Arg Leu Gln Met Gln Gln Leu Gln Gln Asn Asn Ile
 50                  55                  60

Val Tyr Phe Asp Leu Asp Lys Tyr Asp Ile Arg Ser Asp Phe Ala Gln
 65                  70                  75                  80

Met Leu Asp Ala His Ala Asn Phe Leu Arg Ser Asn Pro Ser Tyr Lys
                 85                  90                  95

Val Thr Val Glu Gly His Ala Asp Glu Arg Gly Thr Pro Glu Tyr Asn
                100                 105                 110

Ile Ser Leu Gly Glu Arg Arg Ala Asn Ala Val Lys Met Tyr Leu Gln
                115                 120                 125

Gly Lys Gly Val Ser Ala Asp Gln Ile Ser Ile Val Ser Tyr Gly Lys
                130                 135                 140

Glu Lys Pro Ala Val Leu Gly His Asp Glu Ala Ala Tyr Ser Lys Asn
145                 150                 155                 160

Arg Arg Ala Val Leu Val Tyr
                165

<210> SEQ ID NO 6
<211> LENGTH: 834
<212> TYPE: DNA
<213> ORGANISM: Artificial Sequence
<220> FEATURE:
```

<223> OTHER INFORMATION: DNS-Fragment xIA
<220> FEATURE:
<221> NAME/KEY: misc_feature
<222> LOCATION: (1)..(834)

<400> SEQUENCE: 6

```
caattcgcgc gcgtaacaaa agtgtctata atcacggcag aaaagtccac attgattatt      60
tgcacggcgt cacactttgc tatgccatag cattttatc cataagatta gcggatccta     120
cctgacgctt tttatcgcaa ctctctactg tttctccata cccgtttttt tgggctagaa     180
ataattttgt ttaagaattc taaggaggaa attatatgca actgaacaaa gtgctgaaag     240
ggctgatgat tgctctgcct gttatggcaa ttgcggcagc ttcttccaac aagaacgcca     300
gcaatgacgg cagcgaaggc atgctgggtg ccggcactgg tatggatgcg aacggcggca     360
acggcaacat gtcttccgaa gagcaggctc gtctgcaaat gcaacagctg cagcagaaca     420
acatcgttta cttcgatctg gacaagtacg atatccgttc tgacttcgct caaatgctgg     480
atgcacatgc aaacttcctg cgtagcaacc cgtcttacaa agtcaccgta gaaggtcacg     540
cggacgaacg tggtactccg gaatacaaca tctccctggg tgaacgtcgt gcgaacgccg     600
ttaagatgta cctgcagggt aaaggcgttt ctgcagacca gatctccatc gtttcttacg     660
gtaaagaaaa aacctgcagta ctgggtcatg acgaagcggc atactccaaa aaccgtcgtg     720
cggtactggt ttactaagaa ttgcaagctg gccgacgcgt cccacagccg ccagttccgc     780
tggcggcatt ttaactttct ttaatgaagc cggaaaaatc ccgcgcgcga aggc          834
```

<210> SEQ ID NO 7
<211> LENGTH: 173
<212> TYPE: PRT
<213> ORGANISM: Artificial Sequence
<220> FEATURE:
<223> OTHER INFORMATION: Pal22A
<220> FEATURE:
<221> NAME/KEY: PEPTIDE
<222> LOCATION: (1)..(173)

<400> SEQUENCE: 7

```
Met Gln Leu Asn Lys Val Leu Lys Gly Leu Met Ile Ala Leu Pro Val
1               5                  10                  15

Met Ala Ile Ala Ala Ala Ser Ser Asn Lys Asn Ala Ser Asn Asp Gly
                20                  25                  30

Ser Glu Gly Met Leu Gly Ala Gly Thr Gly Met Asp Ala Asn Gly Gly
            35                  40                  45

Asn Gly Asn Met Ser Ser Glu Glu Gln Ala Arg Leu Gln Met Gln Gln
        50                  55                  60

Leu Gln Gln Asn Asn Ile Val Tyr Phe Asp Leu Asp Lys Tyr Asp Ile
65                  70                  75                  80

Arg Ser Asp Phe Ala Gln Met Leu Asp Ala His Ala Asn Phe Leu Arg
                85                  90                  95

Ser Asn Pro Ser Tyr Lys Val Thr Val Glu Gly His Ala Asp Glu Arg
            100                 105                 110

Gly Thr Pro Glu Tyr Asn Ile Ser Leu Gly Glu Arg Arg Ala Asn Ala
        115                 120                 125

Val Lys Met Tyr Leu Gln Gly Lys Gly Val Ser Ala Asp Gln Ile Ser
    130                 135                 140
```

-continued

```
Ile Val Ser Tyr Gly Lys Glu Lys Pro Ala Val Leu Gly His Asp Glu
145                 150                 155                 160

Ala Ala Tyr Ser Lys Asn Arg Arg Ala Val Leu Val Tyr
                165                 170
```

BACTERIAL STRAIN FOR RELEASING A RECOMBINANT PROTEIN IN A FERMENTATION METHOD

CROSS REFERENCE TO RELATED APPLICATIONS

This application is the U.S. National Phase of PCT Appln. No. PCT/EP2018/068418 filed Jul. 6, 2018, the disclosure of which is incorporated in its entirety by reference herein.

SEQUENCE LISTING

The text file Sequence_listing_C011724_ST25 of size 10 KB created Dec. 21, 2020, filed herewith, is hereby incorporated by reference.

BACKGROUND OF THE INVENTION

1. Field of the Invention

The invention relates to a bacterial strain containing an open reading frame encoding a recombinant protein under the control of a functional promoter, characterized in that the bacterial strain contains an open reading frame encoding a mutated peptidoglycan-associated lipoprotein (Pal protein) under the control of a functional promoter, the Pal protein having been mutated such that it has no membrane anchor for the outer cell membrane of the bacterium. The invention further relates to a plasmid encoding a recombinant protein and the mutated Pal protein and to a method for fermentative production of recombinant proteins using the bacterial strain according to the invention.

2. Description of the Related Art

Recombinant proteins can be produced cost-effectively in bacteria because of their short generation time and the simple handling in comparison with mammalian cell cultures. Owing to its extensively studied genetics and physiology, the Gram-negative enterobacterium *Escherichia coli* is currently the most commonly used organism for production of recombinant proteins. What are particularly attractive are production methods for recombinant proteins in *E. coli* in which the target protein is released directly into the fermentation medium in high yield and in the correct folding, since this avoids complicated cell-disruption and protein-folding processes. A range of *E. coli* strains and processes with *E. coli* strains that achieve a release of recombinant proteins into the culture medium are disclosed in the literature.

i) First of all, there is the possibility of using so-called "leaky" strains. These are to be understood to mean mutants of *E. coli* that have a defect in the outer membrane and therefore partially discharge periplasmic proteins into the culture medium. This is a nonspecific mechanism. An example of such "leaky" mutants are strains having defects in the Tol-Pal complex, for example tol- and pal-deletion mutants. It is known that tol- and pal-deletion mutants discharge cell-endogenous periplasmic proteins into the fermentation medium, such as, for example, alkaline phosphatase PhoA or RNase I. Such strains are extremely sensitive to EDTA, various detergents and antibiotics and exhibit growth defects (Lazzaroni and Portalier 1981, J. Bact. 145, pages 1351-1358; Lazzaroni and Portalier 1992, Mol. Microbiol. 6, pages 735-742; Chen et al. 2014, Microb. Biotechnol. 7, pages 360-370; Bernstein et al. 1972, J. Bacteriol. 112, pages 74-83). Therefore, they are of only limited suitability for culturing under high-cell-density fermentation conditions.

ii) A further approach for achieving the release of recombinant proteins is the expression of a protein which permeabilizes the cell envelope of *E. coli* and thus promotes the release of proteins into the culture medium. The expression of bacteriocin release proteins (BRPs), small lipoproteins which lead to a degradation of the outer membrane and to the lysis of the cells, is well-described. By overexpression of ColE1 BRP (Kil protein) or of cloacin DF13 BRP, it was possible to discharge interleukin-2, β-glucanase, alkaline phosphatase or β-lactamase into the culture medium (Beshay et al. 2007, Biotechnol. Lett. 29, pages 1893-1901; Robbens et al. 1995, Protein Expr. Purif. 6, pages 481-486; Sommer et al. 2010, J. Biotechnol. 145, pages 350-358).

iii) Another approach for destabilizing the cell envelope has been described in Wan and Baneyx (1998, Protein Expr. Purif. 14, pages 13-22). This involved destroying membrane integrity by overexpressing the soluble, C-terminal domain of the TolA protein (TolAIII). This led to a similar phenotype as in tolA-deletion mutants with increased release of the proteins RNase I and alkaline phosphatase from the periplasm into the medium and to sensitivity to deoxycholate (Levengood-Freyermuth et al. 1993, J. Bacteriol. 175, pages 222-228). By overexpression of the TolAIII protein, the release of an OmpA-TEM-β-lactamase protein was distinctly increased. However, the expression of β-lactamase declined by a factor of 1.5-2 in comparison with the control. Furthermore, the vitality of the cells was greatly impaired by expression of TolAIII, just as in tolA mutants. The number of colony-forming units (CFU), as a measure of the vitality of the culture, already declined by a factor of 1000 in a shake flask 3 h after the start of TolAIII expression. In addition, the cells were sensitive to low concentrations of SDS (0.02%), an indication of distinct membrane defects. Such cells are unsuitable for culturing at high cell densities, over a relatively long period required for production of complex, eukaryotic proteins. A further disadvantage of the coexpression of TolAIII is that TolAIII itself can be found in large amounts in the culture supernatant and thus contaminates the outwardly transferred target protein.

It is an object of the present invention to provide a bacterial strain which releases a recombinant protein into the culture medium in an increased yield without a strong cell lysis occurring.

SUMMARY OF THE INVENTION

The foregoing object is achieved by a bacterial strain containing an open reading frame encoding a recombinant protein under the control of a functional promoter, characterized in that it contains an open reading frame encoding a mutated peptidoglycan-associated lipoprotein (Pal protein) under the control of a functional promoter, the mutated Pal protein having been mutated such that it has no membrane anchor for the outer cell membrane of the bacterium.

DETAILED DESCRIPTION OF THE PREFERRED EMBODIMENTS

Figure 1:
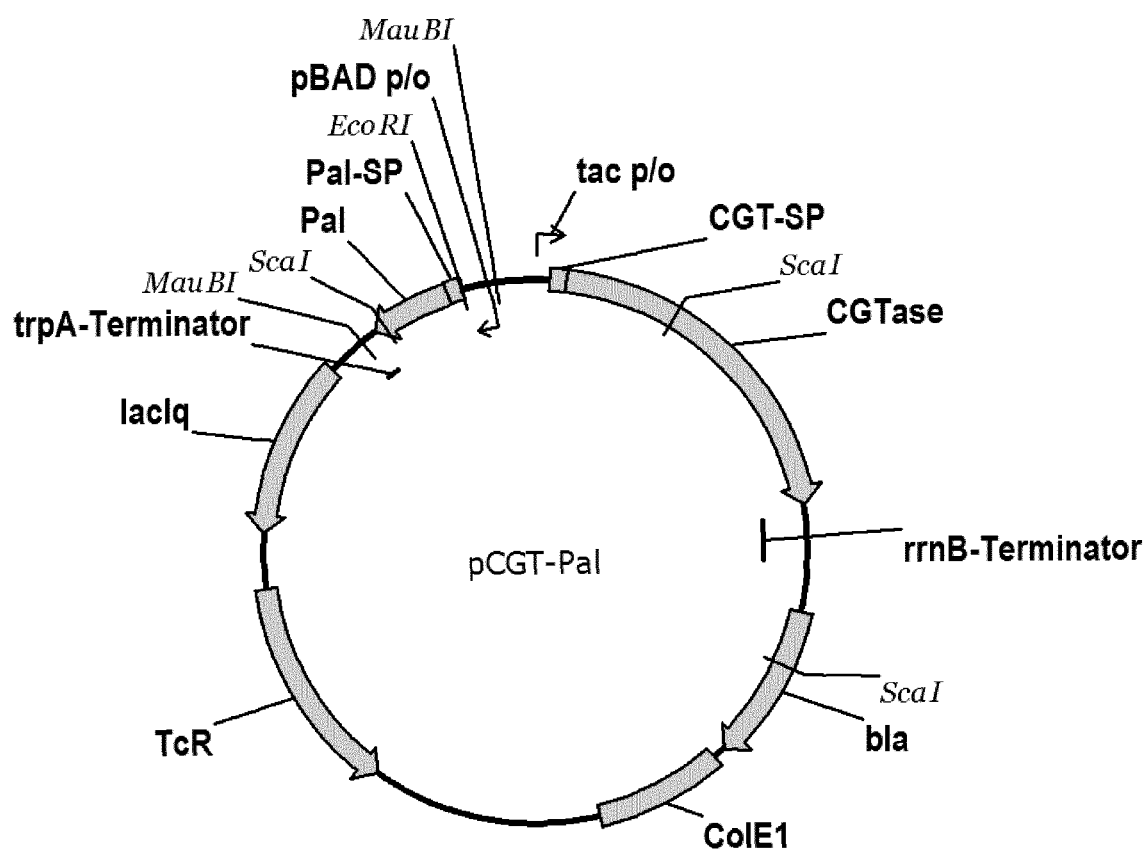
FIG. 1 shows the plasmid map of the plasmid pCGT-Pal.

The use of such a bacterial strain in a fermentation method has the advantage that an additional protein, namely a mutated form of the Pal protein, is expressed together with the recombinant protein. The expression of the mutated Pal protein leads to a limited permeabilization of the outer cell membrane of the bacterium, so that recombinant proteins can be released from the cell without death of the cell. As a result of the improved release, the recombinant proteins can be isolated in an increased yield. The invention provides a corresponding bacterial strain, a method for fermentative production of recombinant proteins using said bacterial strain, and a corresponding plasmid. In this way, it is possible to achieve increased product yields in the culture supernatant compared to the prior art without the occurrence of substantial death of the bacterial cells.

The bacterial strain is preferably characterized in that the bacterial strain Gram-negative, more preferably a bacterial strain of the genus Enterobacteriaceae, and most preferably a strain of the species *Escherichia coli*.

The peptidoglycan-associated lipoprotein (Pal, Pal protein) is a bacterial, periplasmic protein which is anchored in the outer membrane of the bacterial cell via its lipidated N-terminus and interacts with the peptidoglycan layer via the C-terminus. In addition, Pal is a component of the Pal-Tol system (Godlewska et al. 2009, FEMS Microbiol. Lett. 298, pages 1-11) and interacts with various further proteins of the periplasm, for instance lpp and ompA (Cascales et al., 2002, J. Bacteriol. 184, pages 754-759; Godlewska, see above). In technical applications, the Pal protein is, for example, used for anchoring antibody fragments, in the form of a fusion protein composed of Pal protein and antibody fragment, on the cell surface of bacteria (Fuchs et al. 1991, Biotechnology (N Y) 9, pages 1369-1372; Dhillon et al. 1999, Lett. Appl. Microbiol. 28, pages 350-354).

The wild-type Pal gene refers to the form of the Pal gene that arose naturally by evolution and is present in the wild-type bacterial genome. The wild-type Pal gene expresses the wild-type Pal precursor protein, which comprises a signal peptide and the amino acid sequence of the wild-type Pal protein (SEQ ID No. 4). After the signal sequence of 21 amino acids has been cleaved off, the mature wild-type Pal protein from *E. coli* (strain K-12) comprises a sequence of 152 amino acids (see Genbank entry X05123, Uniprot P0A912) and bears at amino acid position 1 the amino acid cysteine, which is highly conserved in bacterial lipoproteins and which is acylated with the membrane anchor (see, for example, Zuckert et al. 2014, Biochimica et Biophysica Acta 1843, pages 1509-1516 or Konovalova and Silhavy 2015, Phil. Trans. R. Soc. B 370: 20150030). By contrast, the mutated Pal protein has no membrane anchor for the outer cell membrane of the bacterium.

Pal precursor protein (precursor form of the Pal protein) refers to the Pal protein which comprises the amino acid sequence of the Pal protein and the signal sequence and does not bear post-translational modifications.

Mature wild-type Pal protein refers to the Pal protein which comprises the amino acid sequence of the wild-type Pal protein and no longer bears a signal sequence, since it has been cleaved off, and in which possible post-translational modifications are present. Such a post-translational modification is, for example, the acylation of the Pal protein with the membrane anchor.

Open reading frame (ORF) refers to that region of the DNA or RNA that is between a start codon and a stop codon and encodes the amino acid sequence of a protein. The ORF is also referred to as a coding region.

ORFs are surrounded by noncoding regions. Gene refers to the DNA segment which contains all the basic information for producing a biologically active RNA. A gene contains the DNA segment from which a single-stranded RNA copy is produced by transcription and the expression signals which are involved in the regulation of this copying process. The expression signals include, for example, at least one promoter, a transcription start site, a translation start site and a ribosome binding site. Furthermore, a terminator and one or more operators are possible as expression signals.

In the case of a functional promoter, the ORF which is under the regulation of said promoter is transcribed into an RNA.

Monocistronic refers to a messenger RNA (mRNA) which contains only one open reading frame.

An operon is a functional unit of DNA that comprises multiple ORFs, a promoter and possibly further expression signals.

The bacterial strain can contain (1) one ORF encoding a recombinant protein, (2) multiple ORFs encoding the same recombinant protein or (3) multiple ORFs encoding different recombinant proteins. Whereas the 2nd possibility is, for example, used for increasing the expression and yield of the recombinant protein, the 3rd possibility is used especially in the expression of proteins which are composed of multiple polypeptides (subunits). One example is the expression of antibody fragments which are subsequently assembled after transport out of the cytoplasm.

Each of these ORFs can be in a separate gene; it is also possible for multiple ORFs to be organized in an operon, i.e., to be regulated by common expression signals.

Moreover, each operon can contain an ORF encoding the mutated Pal protein. Even though one or more ORFs encoding one or more recombinant proteins and the ORF encoding the mutated Pal protein are in an operon, the mutated Pal protein is always expressed as a separate protein and not as a fusion protein, since the ORF encoding the mutated Pal protein is, by definition, distinguished by its own translation start codon and stop codon.

If the recombinant protein is composed of multiple polypeptide chains (subunits), it is preferred that the ORFs of the individual peptide chains (subunits) are organized in an operon.

It is preferred that the ORF encoding the mutated Pal protein is transcribed as monocistronic messenger RNA. This means that the mutated Pal protein is expressed by a separate gene of its own. Said gene is referred to as a mutated Pal gene.

The ORFs encoding the recombinant protein and the mutated Pal protein can be expressed chromosomally or by a plasmid. In the case of separate genes, they can also be expressed by separate plasmids compatible with one another with regard to origin of replication and selection marker. The ORFs are preferably plasmid-encoded.

The ORF used in this invention and encoding the mutated Pal protein contains changes in the amino acid sequence, such as substitutions, deletions and/or insertions, in comparison with the wild-type Pal protein.

According to the present invention, the sequence of the ORF encoding the mutated Pal protein is preferably a DNA sequence which leads to the expression of a mutated Pal protein, which DNA sequence originates from the same organism also used for production of the recombinant proteins.

The origin of the DNA sequence of the ORF according to the invention encoding the mutated Pal protein is not restricted to the bacterial strain used for production of the recombinant protein, so long as the corresponding Pal protein in the nonmutated form is functional in the bacterial strain used for production of the recombinant protein. In this connection, functional means that all biological functions of the Pal protein of the bacterial strain used for production of the recombinant protein can be taken on by the abovementioned Pal protein. In particular, this means that the phenotypical characteristics of a bacterial strain with a chromosomal deletion of the Pal gene can be complemented by an additionally introduced copy of the abovementioned Pal gene.

The term "a/the ORF encoding a recombinant protein" and "a/the recombinant protein", which is used in the singular in the context of this invention, can also mean multiple ORFs and/or multiple different recombinant proteins. Preferably 1 to 3 different recombinant proteins, particularly preferably 1 recombinant protein or 2 different recombinant proteins, are concerned. The cloning and expression of recombinant proteins in bacteria is achieved as described in the prior art. The recombinant protein has, for example, a signal sequence for transport into the periplasm.

The recombinant protein is a protein which the wild-type bacterial genome naturally either does not express at all or expresses in a different amount. The bacterium serves for the production of the recombinant protein, said protein being, according to the invention, released into the culture medium.

To achieve the release of the recombinant protein into the culture medium, it is necessary for both the recombinant protein and the mutated Pal protein to be transported into the periplasm after protein biosynthesis in the cytosol. For transport into the periplasm, it is necessary to link the 5' end of the coding DNA sequence of the protein to be produced in frame with the 3' end of a signal sequence for protein export. Suitable for this purpose are, in principle, all signal sequences which allow a translocation of the target protein with the aid of the Sec or Tat apparatus in the bacterial strain used. Various signal sequences are described in the prior art, for example the signal sequences of the following genes: phoA, ompA, pelB, ompF, ompT, lamB, malE, Staphylococcal protein A, StII and others (Choi and Lee 2004, Appl. Microbiol. Biotechnol. 64, pages 625-635). What is preferred according to the invention for recombinant proteins is the signal sequence of the phoA gene or the ompA gene of *E. coli* or the signal sequence for a cyclodextrin glycosyltransferase (α-CGTase) from *Klebsiella pneumoniae* M5a1 or signal sequences derived therefrom that are disclosed in US 2008/0076157 as SEQ ID No. 1 and 3. Preferably, the mutated Pal protein bears, in its precursor form, the native signal sequence of the Pal protein, as described in Chen and Henning (1987, Eur. J. Biochem. 163, pages 73-77). Preferably, the recombinant protein and the mutated Pal protein bear, in their precursor form, a differing signal sequence, the two signal sequences bringing about protein export.

The expression of the ORFs encoding the mutated Pal protein and the recombinant protein can be controlled by one promoter or different promoters. It is preferred that the ORFs for the mutated Pal protein and for the recombinant protein are under the control of different promoters.

The DNA segment encoding the mutated Pal protein can be first amplified by means of PCR using oligonucleotides as primers and a DNA template encoding the Pal protein, for example genomic DNA isolated from *E. coli*, and then, using common molecular-biology techniques, linked in each case with the DNA molecule comprising the sequence of a signal peptide and generated in an analogous manner, such that an in-frame fusion is formed. Alternatively, it is also possible to produce the entire DNA molecule by means of gene synthesis. Said DNA molecule consisting of the signal sequence in question and the coding sequence of the mutated Pal protein can then either be introduced into a vector, for example a plasmid, or be directly integrated by known methods into the chromosome of the bacterial strain. Preferably, the DNA molecule is introduced into a plasmid, such as, for instance, a derivative of known expression vectors, such as pJF118EH, pKK223-3, pUC18, pBR322, pACYC184, pASK-IBA3 or pET. Plasmids are introduced into the bacterial cells using methods known by a person skilled in the art (transformation).

The plasmids used can bear selection markers. Suitable as selection markers are genes which encode a resistance to antibiotics such as, for example, ampicillin, tetracycline, chloramphenicol, kanamycin or others. Preferably, the plasmid contains a gene, the expression of which mediates tetracycline resistance. Suitable as selection markers are, furthermore, auxotrophic markers which encode an essential gene which has been deleted in the bacterial strain in question that contains the plasmid. If two plasmids are transformed into the cells, preference is given to selecting for the presence of both plasmids using two different antibiotic resistances or two different auxotrophic markers.

Suitable as promoters are all promoters known to a person skilled in the art, such as constitutive promoters such as, for example, the GAPDH promoter or inducible promoters such as, for example, the lac, tac, trc, lambda PL, ara, cumate or tet promoter or sequences derived therefrom. The ORFs encoding the recombinant protein and the ORF encoding the mutated Pal protein can be controlled as an operon by a promoter or be under the control of different promoters. Preferably, the ORFs encoding the recombinant protein and the ORF encoding the mutated Pal protein are controlled by different inducible promoters. Particularly preferably, the recombinant protein is expressed under the control of the tac promoter and the mutated Pal protein is expressed under the control of the ara (arabinose) promoter.

The amino acid sequence of the mutated Pal protein can be produced in a known manner, for example by removing the conserved cysteine residue or introducing other mutations which prevent the modification with a membrane anchor. A person skilled in the art is aware of methods from the literature for checking whether an introduced mutation leads to the mutated Pal protein no longer containing a membrane anchor after expression in a bacterial strain (Hayashi and Wu 1990, J. Bioenerg. Biomembr. 22, pages 451-471; Giam et al. 1984, Eur. J. Biochem. 141, pages 331-337; Lazzaroni and Portalier 1992, see above; Mizuno 1979, J. Biochem. 86, pages 991-1000).

In a preferred embodiment, the bacterial strain is characterized in that the ORF encoding the mutated Pal protein has been mutated such that it encodes a mutated Pal protein which has been mutated at one or more of amino acid positions 1 to 6, preferably 1 to 4 and more preferably 1 to 2. In this connection, the amino acid position refers to the amino acids which follow the signal sequence, i.e., amino acid position 1 is the first amino acid after the signal sequence.

Preferably, the mutation is a deletion (absence of amino acids) or substitution (exchange of amino acids), most preferably a deletion.

Most preferably, the bacterial strain is characterized in that the ORF encoding the mutated Pal protein has been mutated such that it encodes a mutated Pal protein in which the N-terminal cysteine residue has been substituted.

In an additionally preferred embodiment, the bacterial strain is characterized in that the ORF encoding the mutated Pal protein has been mutated such that it encodes a mutated Pal protein in which the N-terminal cysteine residue is absent. Preferably, the amino acid is deleted at position 1, most preferably the cysteine residue.

N-terminus or amino-terminus refers to the end of the Pal protein that has a free amino group ($NH_2$). The N-terminal cysteine residue is the cysteine residue at amino acid position 1 after the signal sequence.

Most preferably, the amino acid sequence of the mutated Pal protein is the sequence which is specified in SEQ ID No. 7 (Pal22A) and in which the N-terminal cysteine has been exchanged for the amino acid alanine, with the result that an alanine follows the first 21 amino acids of the signal sequence.

In a preferred embodiment, the bacterial strain is characterized in that the ORF encoding the mutated Pal protein has been mutated such that it encodes a mutated Pal protein in which amino acids 1 to 6, preferably 1 to 4 and more preferably 1 to 2 are absent. Most preferably, the amino acid sequence of the mutated Pal protein is the sequence which is specified in SEQ ID No. 5 (Pal$\Delta_{22-27}$) and in which an alanine follows the first 21 amino acids of the signal sequence. The sequence after the signal peptide of the mutated Pal protein is identical to amino acids 7-152 of the mature wild-type Pal protein from E. coli (see SEQ ID No. 4 for the amino acid sequence of the wild-type protein).

Preferably, the recombinant protein is a heterologous protein. Heterologous proteins are to be understood to mean proteins which do not belong to the proteome, i.e., the entire natural set of proteins, of the bacterial strain, preferably an E. coli K12 strain. All proteins occurring naturally in the bacterial strain used, for example in the E. coli K12 strain, can be derived from the known genome sequences (e.g., from the Genbank entry under accession No. NC_000913 for E. coli K12).

Particularly preferred as heterologous proteins are eukaryotic proteins which contain one or more disulfide bonds. Especially preferred are eukaryotic proteins which, in their functional form, are present as dimers or multimers.

The most important heterologous protein classes include antibodies and fragments thereof, cytokines, growth factors, protein kinases, protein hormones, lipocalins, anticalins, enzymes, binding proteins and molecular scaffolds and proteins derived therefrom. Examples of said protein classes are, inter alia, heavy-chain antibodies and fragments thereof (e.g., nanobodies), single-chain antibodies, interferons, interleukins, interleukin receptors, interleukin receptor antagonists, G-CSF, GM-CSF, M-CSF, leukemia inhibitors, stem cell growth factors, tumor necrosis factors, growth hormones, insulin-like growth factors, fibroblast growth factors, platelet-derived growth factors, transforming growth factors, hepatocyte growth factors, bone morphogenetic factors, nerve growth factors, brain-derived neurotrophic factors (BDNF), glial cell line-derived neurotrophic factors, angiogenesis inhibitors, tissue plasminogen activators, blood coagulation factors, trypsin inhibitors, elastase inhibitors, complement constituents, hypoxia-induced stress proteins, proto-oncogenic products, transcription factors, virus-constitutive proteins, proinsulin, prourokinase, erythropoietin, thrombopoietin, neurotrophin, protein C, glucocerebrosidase, superoxide dismutase, renin, lysozyme, P450, prochymosin, lipocortin, reptin, serum albumin, streptokinase, tenecteplase, CNTF and cyclodextrin glycosyltransferases.

Examples of proteins derived from molecular scaffolds are, inter alia, evibodies (derived from CTLA-4), affibodies (protein A of S. aureus), avimers (of human A domain family), transbodies (of transferrin), DARPins (of ankyrin repeat protein), adnectin (of fibronectin III), peptide aptamers (of thioredoxin), microbodies (of microprotein), affilins (of ubiquitin), α-crystallin, charybdotoxin, tetranectin, PDZ domain of the RAS-binding protein AF-6, Kunitz-type domain of protein inhibitors.

Preferably, the bacterial strain is characterized in that it additionally contains the wild-type Pal gene encoding the peptidoglycan-associated lipoprotein (Pal). Most preferably, the wild-type Pal gene is under the control of a functional promoter.

The invention further provides a plasmid containing an open reading frame encoding a recombinant protein under the control of a functional promoter, characterized in that it contains an open reading frame encoding a signal peptide and a mutated Pal protein under the control of a functional promoter, the Pal protein having been mutated such that it has no membrane anchor for the outer cell membrane of the bacterium.

The preferred and particularly preferred features mentioned for the bacterial strain according to the invention also apply to the features mentioned in the plasmid according to the invention, wherein the preferred and particularly preferred embodiments mentioned for the bacterial strain according to the invention are also respectively preferred or particularly preferred in the plasmid.

Similarly, the mentioned definitions and preferred embodiments apply to the ORF encoding a signal peptide and a mutated Pal protein and to the ORF encoding the recombinant protein.

For example, one or more ORFs encoding one or more recombinant proteins can be in one operon. Preferably, the ORF encoding the mutated Pal protein is in a separate gene. This means that the mutated Pal protein and recombinant proteins can be expressed independently of one another. In the particularly preferred case of the promoter (s) of the recombinant protein (s) being different from the promoter of the mutated Pal protein and differently inducible, the plasmid has the particular advantage that, upon transformation of bacteria with said plasmid, it is possible to choose the optimal time point for the expression of the proteins independently of one another.

The introduction of the plasmid according to the invention into the bacterial strain using methods known to a person skilled in the art and the expression of the recombinant protein and of the mutated Pal protein by said plasmid has the advantage that the release of the recombinant proteins from the cells of the bacterial strain is improved and that they can be isolated in an increased yield.

In comparison with chromosomal integration of the ORFs encoding the recombinant protein and the mutated Pal protein, the advantage of the use of plasmids is that the plasmid-bearing cells of the bacterial strain have a selection advantage and can be selected by standard methods.

Since each plasmid contains at least one origin of replication (ORI), a further advantage is that plasmids replicate autonomously. Furthermore, it is of particular advantage that plasmids can be present in high copy number in the cells of the bacterial strain and are inherited.

The invention further provides a method for fermentative production of recombinant proteins, characterized in that a bacterial strain according to the invention is cultured in a fermentation medium, the fermentation medium is removed from the cells after the fermentation, and recombinant proteins are isolated from the fermentation medium.

The cells of the bacterial strain that have been transformed by chromosomal integration or with one or two expression plasmids are cultured by customary methods known to a person skilled in the art in a shake flask or in a bioreactor (fermenter).

Possibilities as fermentation media (growth media, culture media) are, in principle, all common media known to a person skilled in the art for culturing bacteria. In this connection, it is possible to use complex media or minimal salts media to which a particular proportion of complex components, such as, for example, peptone, tryptone, yeast extract, molasses or corn steep liquor, is added. Furthermore, it is possible to add to the medium further components, such as vitamins, salts, amino acids and trace elements, which improve cell growth.

The fermentation is preferably carried out in a conventional bioreactor, for example, a stirred tank, a bubble column fermenter or an airlift fermenter. Particular preference is given to a stirred tank fermenter.

The fermentation involves culturing the cells of the protein production strain in a growth medium with ongoing monitoring and precise control of various parameters, such as, for example, nutrient feed, oxygen partial pressure, pH and temperature of the culture. The culturing period is preferably 24-65 h.

The primary carbon source used for the fermentation can, in principle, be all sugars, sugar alcohols or organic acids or salts thereof that are utilizable by the cells. In this connection, preference is given to using glucose, lactose, arabinose or glycerol. Particular preference is given to glucose and arabinose. Also possible is a combined feeding of multiple different carbon sources. In this case, the carbon source can be initially charged in full in the fermentation medium at the start of fermentation, or nothing or only a portion of the carbon source is initially charged at the start and the carbon source is fed over the course of the fermentation. Particularly preferred in this connection is one embodiment in which a portion of the carbon source is initially charged and a portion is fed. Particularly preferably, the carbon source glucose is initially charged in a concentration of 10-30 g/l, and the feeding is started when the concentration has dropped to less than 5 g/l in the course of the fermentation and is configured such that the concentration is held below 5 g/l.

If the expression of the recombinant protein and/or of the mutated Pal protein is controlled by an inducible promoter, the expression is induced by addition of the promoter-corresponding inducer to the fermentation batch. Suitable as inducers are, for example, arabinose, lactose, IPTG, tetracycline or cumate. The inducer can be metered in at any desired time point during the fermentation as a single or multiple dose. Alternatively, the inducer can be added continuously. Preferably, the expression of the recombinant protein is induced by addition of IPTG and the expression of the mutated Pal protein is induced by addition of arabinose. Particularly preferably, IPTG is metered in as a single dose and the induction of the expression of the mutated Pal protein is configured such that a mixture of glucose and arabinose is fed at a time point after the glucose concentration has dropped below 5 g/l. In this connection, the arabinose proportion of the mixture is preferably between 33% by weight and 66% by weight; particularly preferably, it is 33% by weight.

The expression of the mutated Pal protein is preferably induced in the culturing phase in which there are only a few to no more cell divisions, i.e., just before or at the start of the stationary phase of the growth curve. This time point is determined by an only little to absolutely no rise in cell density, determined as $OD_{600}$ value or CDW value (see below).

Preferably, the medium in the fermenter is stirred before inoculation and sparged with sterilized compressed air; in this connection, the oxygen content is calibrated to 100% saturation and a target value for the $O_2$ saturation during the fermentation is chosen, which is between 10% and 70%, preferably between 20% and 60% and particularly preferably at 30% of this value. After the $O_2$ saturation has fallen below the target value, a regulation cascade starts in order to bring the $O_2$ saturation back to the target value, it being possible to adjust gas supply and stirring speed.

The pH of the culture is preferably between pH 6 and pH 8. Preferably, a pH between 6.5 and 7.5 is set; particularly preferably, the pH of the culture is held between 6.8 and 7.2.

The temperature of the culture is preferably between 15° C. and 45° C. Preference is given to a temperature range between 20° C. and 40° C., particular preference is given to a temperature range between 25° C. and 35° C., and very particular preference is given to the temperature of 30° C.

According to the invention, the fermentation medium is removed from the cells after the fermentation, and recombinant proteins are isolated from the fermentation medium. This can be done by customary methods, as are known in the prior art. Customarily, the cells are, in a first step, removed from the recombinant proteins released into the culture medium by means of separation methods such as centrifugation or filtration. The recombinant proteins can then, for example, be concentrated by ultrafiltration.

The expression of the mutated Pal protein improves the release of recombinant proteins into the culture supernatant. As a result of the improved release, recombinant proteins can be isolated in an increased yield.

Increased yield is to be understood to mean that what is released into the culture medium is preferably at least 110%, more preferably at least 150% and especially at least 200% of the amount of recombinant protein that can be produced according to the current state of the art using a wild-type bacterial strain containing a gene for the recombinant protein or a wild-type bacterial strain containing a gene for the recombinant protein and expressing additionally a protein for destabilization of the bacterial cell envelope. This means that the yield of recombinant protein which is released into the culture medium is preferably at least 1.1 times, more preferably at least 1.5 times and especially at least 2 times as high as the yield which can be achieved with corresponding bacterial strains from the prior art.

For instance, Example 1 shows that, in comparison with the corresponding wild-type bacterial strain or a TolAIII-expressing bacterial strain, more than 2-3 times as much CGTase can be produced in the cell supernatant in the same culture volume when PalΔ22-27 or Pal22A is expressed (see Table 1). In Example 2 as well, the production of CGTase by the Pal4Δ22-27-expressing mutant is, compared to the corresponding wild-type bacterial strain or TolAIII-expressing bacterial strain, increased by a factor of 2-3 (see Table 2). Example 3 (see Table 3) similarly confirms a distinct increase.

A further advantage of the described Pal mutants is that, at the same time, the cell lysis in the case of a culture period of 5-24 h is increased only slightly compared to corresponding wild-type cells. Wan and Baneyx (1998, see above) show that TolAIII overproduction leads, just after a few hours, to a CFU count approx. lower by a factor of 1400-3000 in comparison with noninduced cells and conclude that the long-term viability of the bacterial cells distinctly drops owing to the influence on the outer membrane. By contrast, 24 h after induction of the expression of the mutated PalΔ22-27 protein, the CFU count only drops by a factor of 2 in comparison with the corresponding wild-type bacterial strain (see Example 3).

With the aid of the coexpression of the mutated Pal protein in a bacterial strain, preferably in E. coli, it is also possible to produce Fab antibody fragments extracellularly. In this case, the bacterial cell must simultaneously synthesize the corresponding fragments of the light chain, which comprises the domains VL and CL, and of the heavy chain, which comprises the domains VH and CH1, of the antibody and then secrete them into the periplasm. Outside the cytoplasm, the two chains then assemble to form the functional Fab fragment. The corresponding ORFs can be in different genes. It is preferred that the ORFs encoding antibody fragments of the light and heavy chain are organized in an operon. As a result of simultaneous production of the Pal protein mutated according to the invention, the heavy and the light chain of the antibody are released into the fermentation medium in an increased concentration.

The method has the major advantage that it is suitable for producing recombinant proteins which require a long culture period and for high-cell-density fermentation. As a result, it is possible to produce complex, eukaryotic proteins as recombinant proteins.

Preferably, the method is characterized in that the recombinant proteins are purified from the fermentation medium after the removal of the fermentation medium.

Recombinant proteins can be further purified via standard methods such as precipitation or chromatography. Particular preference is given here to methods such as affinity chromatography, which utilizes the already correctly folded native conformation of the protein.

Preferably, the method is characterized in that the expression of the mutated Pal protein is induced. This means that either the expression of the mutated Pal protein or the expression of the recombinant protein and the expression of the mutated Pal protein is induced. This means that, in this preferred embodiment, the expression of the mutated Pal protein is in any case under the control of an inducible promoter. By contrast, the expression of the recombinant protein can be under the control of a constitutive or an inducible promoter.

Particularly preferably, both the ORF encoding the recombinant protein and the ORF encoding the mutated Pal protein are under the control of an inducible promoter, especially preferably of differently inducible promoters. Therefore, the expression of the mutated Pal protein and that of the recombinant protein is preferably inducible.

Since the promoters of the genes encoding the recombinant protein and the mutated Pal protein can preferably be induced independently of one another, it is possible to choose independently of one another the optimal time point for the expression of the recombinant protein and for the expression of the mutated Pal protein.

By using inducible promoters, it is possible to induce the expression of the corresponding proteins at any desired time point of the fermentation. Preferably, the expression of the mutated Pal protein is induced after the induction of the expression of the recombinant protein. Particularly preferably, the expression of the mutated Pal protein is induced at least 1 hour, especially preferably at least 2 hours, further particularly preferably 15 to 24 hours and specifically preferably 19 hours after the induction of the expression of the recombinant protein.

The induction of the expression of the recombinant protein and of the mutated Pal protein is triggered by addition of the inducer to the culture medium, it being necessary to choose the inducer in line with the gene used. In the preferred embodiment in which the mutated Pal gene contains an arabinose (ara) promoter, the expression of the mutated Pal protein is induced by addition of the inducer arabinose to the culture. In the preferred embodiment in which the recombinant gene contains a tac promoter, the expression of the recombinant protein is induced by addition of the inducer lactose or of the lactose analog IPTG to the culture.

According to the invention, even after induction of the expression of the mutated Pal protein and further culture of the cells, the cell density of the strain is comparable to a bacterial strain which does not express a mutated Pal protein. In particular, a strong decrease in optical density due to cell lysis does not occur and only a slight decrease in live cell count, measured as colony-forming units (CFUs), occurs.

The higher the measured optical density (OD), the higher the cell density. Bacterial strains having a destabilized cell envelope generally exhibit relatively high cell lysis. In the case of relatively high cell lysis, the cell density drops and consequently so does the OD value.

The invention has the advantage that recombinant proteins are released into the culture medium without the occurrence of strong lysis of the cells of the bacterial strain. The method according to the invention is therefore distinguished by being suitable both for producing complex, eukaryotic proteins having a correspondingly long culture period and for high-cell-density fermentation.

In the context of this invention, fermentations in which cell dry weights >50 g/l are reached are considered to be high-cell-density fermentation. This is also reflected in the literature (Bruschi et al. 2014, Microb. Cell Fact. 13:99; Shokri and Larsson 2004, Microb. Cell Fact. 3:9; Knabben et al. 2010, J. Biotechnol. 150, pages 73-79).

A long culture period means that the culturing time is at least 24 h, preferably at least 48 h and more preferably at least 72 h.

In the context of the invention, a relatively low (or only slightly increased or nonstrong) cell lysis means that there is only a little to absolutely no reduction in the $OD_{600}$ value, CDW value or the value for the live cell count of the culture of the bacterial strain that is determined in the case of a culture period of preferably 5-24 h after induction of the expression of the mutated Pal protein in comparison with the wild-type bacterial strain which does not bear said Pal mutation. The bacterial strains expressing the mutated Pal protein have a major advantage, especially in relation to the culture of bacterial strains containing modifications to destabilize their cell envelope, the cell lysis of which is distinctly increased, as shown by Wan and Baneyx (1998, see above) for cells expressing the TolAIII protein.

Therefore, a cell culture from the fermentation method according to the invention is preferably characterized in that it has, 5 to 24 hours, more preferably 7 hours, after induction of the expression of the mutated Pal protein, an optical density determined at 600 nm ($OD_{600}$) that is lower by not more than 20%, more preferably not more than 10% and especially not more than 58, than the $OD_{600}$ value of a cell culture at the same time point from a fermentation method which only differs from the method according to the invention in that a bacterial strain is cultured which only differs from the bacterial strain according to the invention in that it does not contain the ORF encoding the mutated Pal protein. The optical density of the cell culture at 600 nm is determined by spectrophotometry.

The optical density of the cell culture determined with the aid of a spectrophotometer at 600 nm is dependent on the quantity of cells per unit of volume (cell concentration, cell density), which is in turn a measure of cell division activity and a measure of cell lysis, with cell lysis leading to a decrease in cell density.

Alternatively, cell weight can also be determined as cell dry weight (CDW) by isolating a defined quantity of culture by filtration or centrifugation, preferably centrifugation, and subsequently drying and weighing it.

A further alternative which allows a comparison of the vitality of the bacterial strain expressing the mutated Pal protein with the bacterial strain not expressing a mutated Pal protein is the determination of the live cell count as "colony-forming units" (CFU) based on a defined culture volume. The experimental procedure is described in Wan and Baneyx (1998, see above). The unit CFU specifies the propagatable cells in the culture. The live cell count in the case of a bacterial strain expressing the mutated Pal protein and a recombinant protein is reduced by at most a factor of 100, preferably by at most a factor of 10, more preferably by at most a factor of two, compared to a bacterial strain which does not express a mutated Pal protein.

By contrast, Wan and Baneyx (1998, see above) state in Table 2 that, 3 hours after induction of TolAIII expression with IPTG, the live cell count determined as number of CFU per ml further increases in the wild-type bacterial strain, whereas it is distinctly reduced in the TolAIII-expressing bacterial strain. The authors conclude that although TolAIII overexpression has a relatively small influence on bacterial growth in the logarithmic growth phase of the bacterial strain, the viability of the bacterial cells distinctly drops in the longer term owing to permeabilization of the outer cell membrane.

The but negligible influence on cell integrity by the expression of the mutated Pal protein is a further significant advantage of the invention. Moreover, as a result of the preferred cloning of the ORF encoding the mutated Pal protein under an inducible promoter, it is possible to control the expression of the mutated Pal protein and to thus narrowly limit the culture time in which the desired effect occurs, and this in turn limits potential impacts on the vitality of the bacterial cells.

The abbreviations used in the figures represent DNA regions encoding the following functions:
tac p/o: tac promoter/operator
pBAD p/o: arabinose promoter/operator
bla: β-lactamase gene (ampicillin resistance)
TCR: tetracycline resistance
lacIq: repressor of the tac promoter
cgt-SP: signal peptide of CGTase
CGTase: cyclodextrin glycosyltransferase
ColE1: origin of replication
phoA-SP: phoA signal peptide
AFA-SP: derivative of the signal peptide of CGTase
rrnB terminator: terminator region of the rrnB gene
trpA terminator: terminator region of the trpA gene
Pal: peptidoglycan-associated lipoprotein
Pal-SP: signal peptide of Pal
TolAIII: domain of the TolA protein
OmpA-SP: signal peptide of OmpA
HisTag: histidine tag
light chain: antibody fragment comprising the domains VL and CL
heavy chain: antibody fragment comprising the domains VH and CH1
ScaI/MauBI/EcoRI: restriction sites of the corresponding restriction endonucleases

EXAMPLES

The invention is described in more detail hereinbelow with reference to example embodiments, without being limited thereby.

All the molecular-biology methods used, such as polymerase chain reaction (PCR), gene synthesis, isolation and purification of DNA, modification of DNA by restriction enzymes and ligase, transformation, etc., were carried out in the manner known to a person skilled in the art, described in the literature or recommended by the respective manufacturers.

Figure 4:
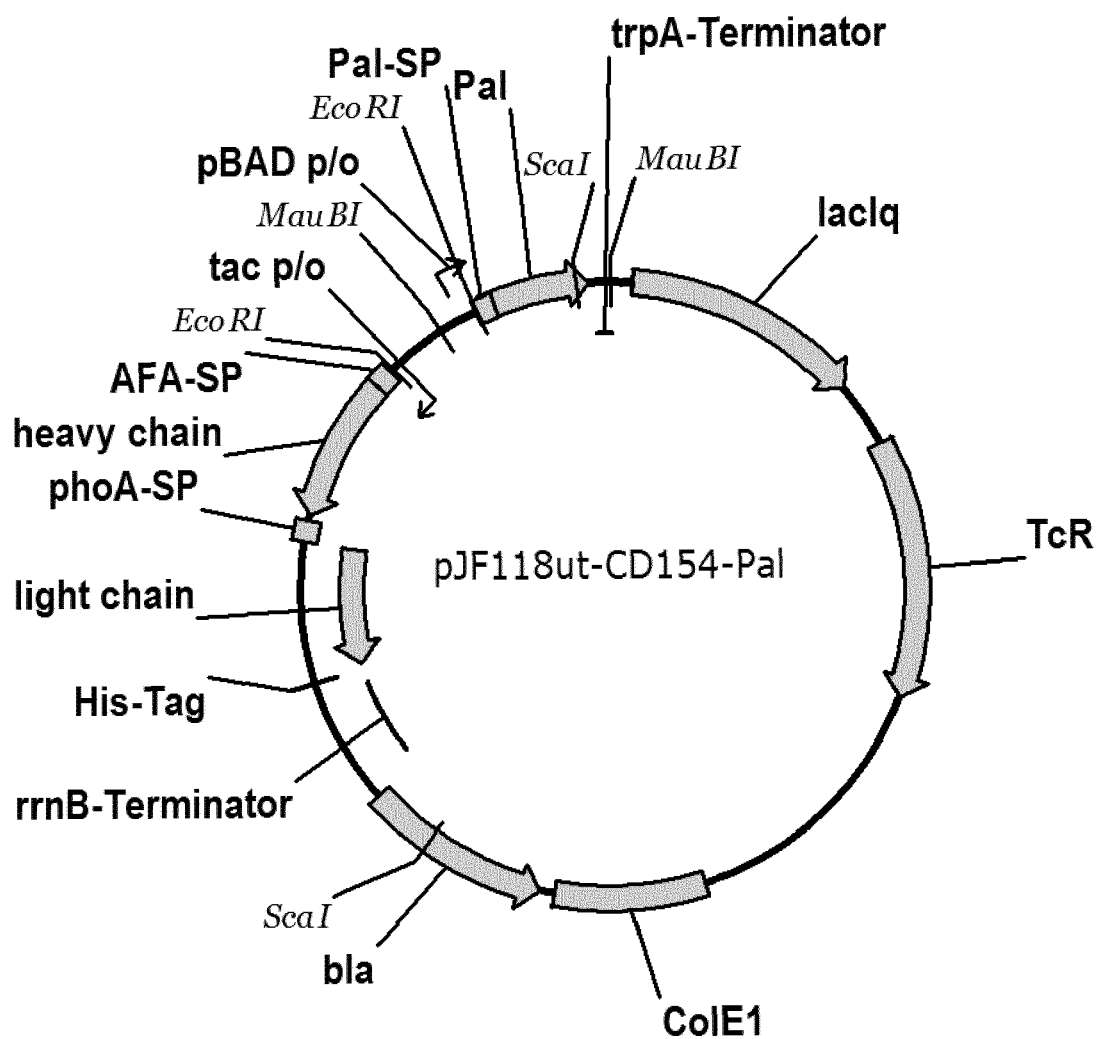
FIG. 4 shows the plasmid map of the plasmid pJF118ut-CD154-Pal.

Description of the Plasmids:
pCGT:
The production of the plasmid pCGT is described in Example 4 of US 2008/0254511 A1, and the plasmid map is specified in FIG. 4 of US 2008/0254511 A1.

Essentially, the plasmid contains not only the gene for resistance to tetracycline, but also, inter alia, the structural gene of the cyclodextrin glycosyltransferase (CGTase) from *Klebsiella pneumoniae* M5a1 including the native CGTase signal sequence. The expression of the CGTase gene is under the control of the tac promoter.

pCGT-Pal:
To obtain pCGT-Pal (see FIG. 1 for the plasmid map), a DNA fragment was produced by means of gene synthesis by eurofins Genomics. Said DNA fragment xI (specified in SEQ ID No. 1) contained:
nucleotides 1136-1304 from GenBank entry X81837.1 containing the arabinose promoter (pBAD promoter) and also the operators O1 and I2+I1 and the CAP binding site (nucleotides 10-178 of SEQ ID No. 1),
the Shine-Dalgarno sequence (nucleotides 203-208 of SEQ ID No. 1) and
a nucleotide fragment encoding a fusion of
  i the signal sequence of the peptidoglycan-associated lipoprotein from *E. coli* K12 (nucleotides 136-198 from GenBank entry X05123.1 encoding amino acids –21 to –1, nucleotides 216-278 of SEQ ID No. 1),
  ii nucleotides 217-654 from GenBank entry X05123.1 encoding amino acids 7-152 of the peptidoglycan-associated lipoprotein from *E. coli* K12 (nucleotides 279-716 of SEQ ID No. 1) and
  iii the terminator of the trpA gene from *E. coli* (nucleotides 749-774 of SEQ ID No. 1).

Figure 5:
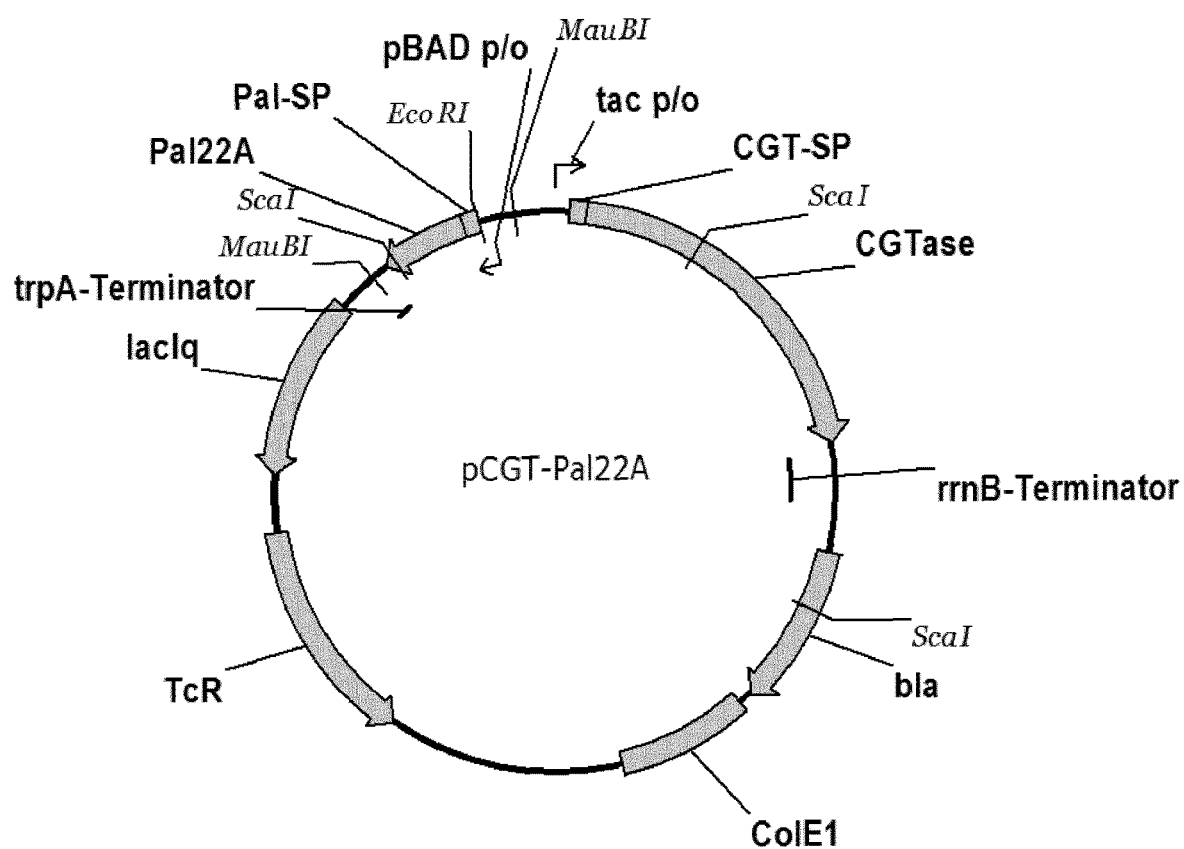
FIG. 5 shows the plasmid map of the plasmid pCGT-Pal22A.

Said DNA fragment xI was cut using the restriction enzyme MauBI and ligated with the expression vector pCGT, which had been cut using the same restriction enzyme. The cloning was done in an undirected manner; however, preference was given to working with the plasmid in which the DNA fragment was inserted in the opposite reading direction to the gene encoding the CGTase, with verification carried out via the restriction pattern of the restriction enzyme ScaI and sequencing. Said plasmid was referred to as pCGT-Pal and encodes the protein Pal422-27, which is synonymously also designated PalD22-27 (specified in SEQ ID No. 5).

pCGT-Pal22A:

To obtain pCGT-Pal22A (see FIG. 5 for the plasmid map), a DNA fragment was produced by means of gene synthesis by eurofins Genomics. Said DNA fragment xIA (specified in SEQ ID No. 6) contained:

nucleotides 1136-1304 from GenBank entry X81837.1 containing the arabinose promoter (pBAD promoter) and also the operators O1 and I2+I1 and the CAP binding site (nucleotides 10-178 of SEQ ID No. 6), the Shine-Dalgarno sequence (nucleotides 203-208 of SEQ ID No. 6) and a nucleotide fragment encoding a fusion of
i the signal sequence of the peptidoglycan-associated lipoprotein from *E. coli* K12 (nucleotides 136-198 from GenBank entry X05123.1 encoding amino acids −21 to −1, nucleotides 216-278 of SEQ ID No. 6),
ii amino acids 1-152 of the peptidoglycan-associated lipoprotein from *E. coli* K12 (cf. GenBank: X05123.1, nucleotides 279-734 of SEQ ID No. 6), wherein the amino acid cysteine at position 1 has been exchanged for an alanine, and
iii the terminator of the trpA gene from *E. coli* (nucleotides 767-792 of SEQ ID No. 6).

Said DNA fragment xIA was cut using the restriction enzyme MauBI and ligated with the expression vector pCGT, which had been cut using the same restriction enzyme. The cloning was done in an undirected manner; however, preference was given to working with the plasmid in which the DNA fragment was inserted in the opposite reading direction to the gene encoding the CGTase, with verification carried out via the restriction pattern of the restriction enzyme ScaI and sequencing. Said plasmid was referred to as pCGT-Pal22A and encodes the protein Pal22A (specified in SEQ ID No. 7).

pCGT-TolAIII:

The overexpression of TolAIII corresponds to the prior art (Wan and Baneyx 1998, see above); therefore, pCGT-TolAIII was chosen as a comparative example representative of the prior art, in which the outer cell envelope of a bacterium containing this plasmid and expressing TolAIII is destabilized and the release of recombinant proteins is increased as a result.

Figure 2:
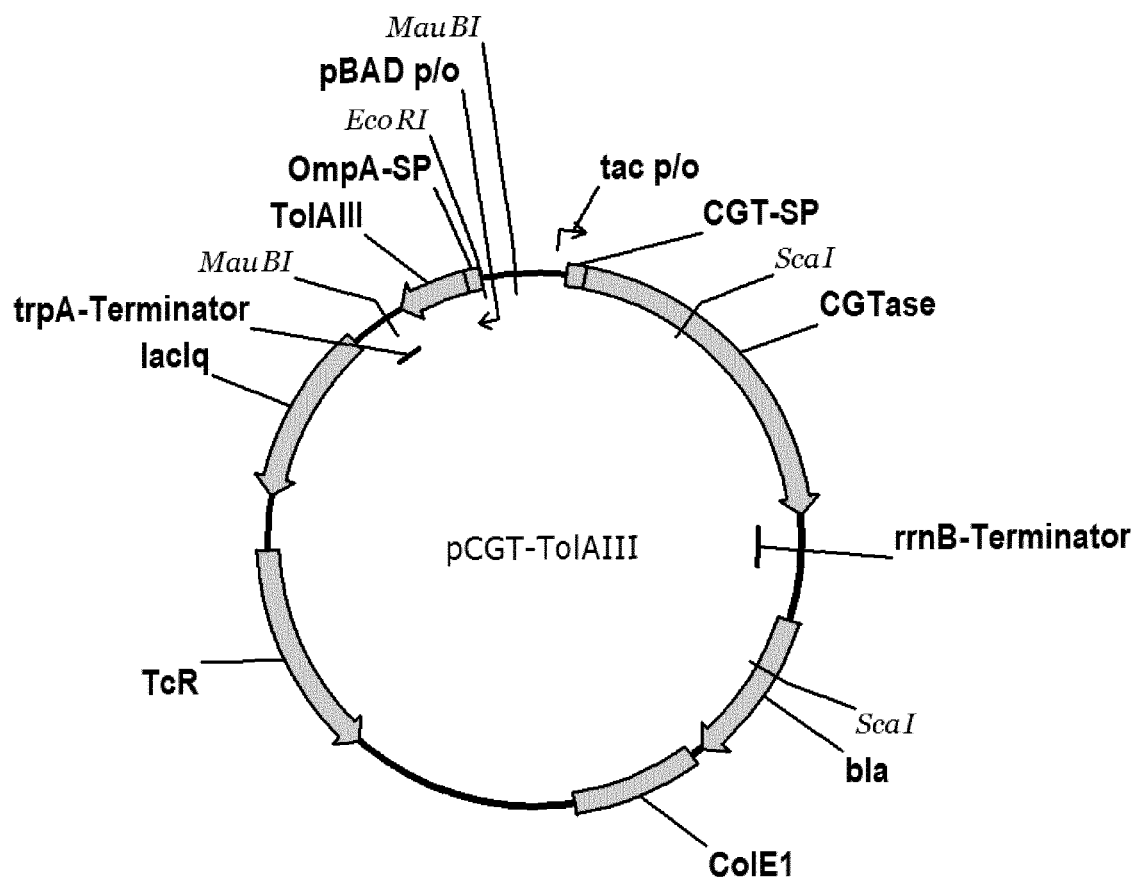
FIG. 2 shows the plasmid map of the plasmid pCGT-TolAIII.

To obtain pCGT-TolAIII (see FIG. 2 for the plasmid map), a DNA fragment was produced by means of gene synthesis by eurofins Genomics. Said DNA fragment xII (specified in SEQ ID No. 2) contained:

nucleotides 1136-1304 from GenBank entry X81837.1 containing the arabinose promoter (pBAD promoter) and also the operators O1 and I2+I1 and the CAP binding site (nucleotides 10-178 of SEQ ID No. 2), the Shine-Dalgarno sequence (nucleotides 203-208 of SEQ ID No. 2) and a nucleotide fragment encoding a fusion of
i the signal sequence of ompA from *E. coli* K12 (nucleotides 216-278 of SEQ ID No. 2),
ii amino acids 291-421 of the TolA protein from *E. coli* K12 (encoding TolAIII, nucleotides 279-671 of SEQ ID Nr. 2) and
iii the terminator of the trpA gene from *E. coli* (nucleotides 714-729 of SEQ ID No. 2).

Said DNA fragment xII was cut using the restriction enzyme MauBI and ligated with the expression vector pCGT (see above), which had been cut using the same restriction enzyme. The cloning was done in an undirected manner; however, preference was given to working with the plasmid in which the DNA fragment was inserted in the opposite reading direction to the gene encoding the CGTase, with verification carried out via the restriction pattern of the restriction enzymes ScaI and EcoRI or sequencing. Said plasmid was referred to as pCGT-TolAIII.

pJF118ut-CD154:

The plasmid pJF118ut described in US 2008/076157 A was used as the starting vector for the cloning and expression of the genes of the Fab fragment of the humanized monoclonal anti-CD154 antibody 5c8, the sequence of which is published in Karpusas et al. 2001 (Structure 9, pages 321-329). pJF118ut is a derivative of the known expression vector pKK223-3 (Amersham Pharmacia Biotech) and deposited at the DSMZ-German Collection of Microorganisms and Cell Cultures GmbH (Braunschweig) under the number DSM 18596.

Figure 3:
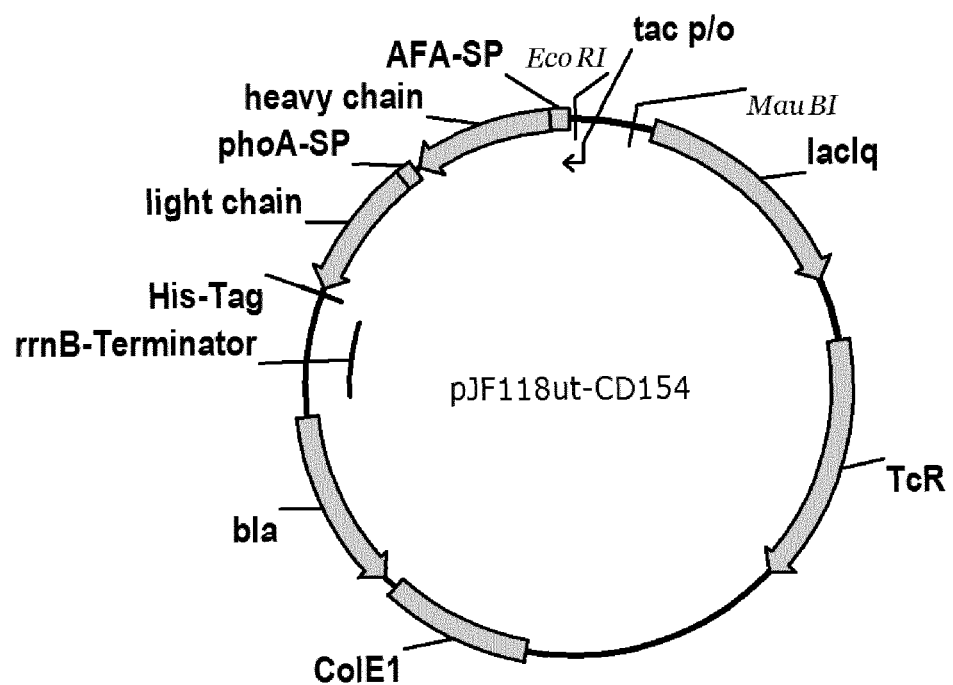
FIG. 3 shows the plasmid map of the plasmid pJF118ut-CD154.

To obtain pJF118ut-CD154 (see FIG. 3 for the plasmid map), a DNA fragment was produced by means of gene synthesis by eurofins Genomics. Said DNA fragment xIII (specified in SEQ ID No. 3) comprised a fusion consisting of:

i the signal sequence disclosed in US 2008/076157 under SEQ ID No. 2 and derived from the signal sequence of a CGTase from *Klebsiella pneumoniae* M5a1 (nucleotides 25-114 of SEQ ID No. 3) and
ii the reading frame for the heavy chain ($V_H$-$C_H$1 domains) of the Fab fragment of the humanized monoclonal anti-CD154 antibody 5c8, encoding amino acids 1-221 of the sequence published in Karpusias et al. 2001 in FIG. 3 (nucleotides 115-777 of SEQ ID No. 3),
iii the phoA signal sequence (nucleotides 800-862 of SEQ ID No. 3),
iv the reading frame for the light chain ($V_L$-$C_L$ domains) of the Fab fragment of the humanized monoclonal anti-CD154 antibody 5c8, as published by Karpusias et al. 2001 in FIG. 3 (nucleotides 863-1516 of SEQ ID No. 3) and
v nucleotides 1517-1546 of SEQ ID No. 3, encoding a linker of 4 amino acids in length and a hexahistidine tag.

Said DNA fragment xIII was cut using the restriction enzymes EcoRI and PdmI and ligated with the expression vector pJF118ut, which had been cut using EcoRI and SmaI. The resulting plasmid, in which the expression of the genes for the heavy and light chain of the Fab fragment was under the control of the tac promoter, was designated pJF118ut-CD154.

pJF118ut-CD154-Pal:

The DNA fragment xI encoding the Pal variant under the control of the arabinose promoter and flanked by the trpA terminator, as described above for pCGT-Pal, was inserted into the plasmid pJF118ut-CD154 via the MauBI restriction site. The cloning was done in an undirected manner; however, preference was given to working with the plasmid in which the DNA fragment xI was inserted in the opposite reading direction to the DNA fragment XIII encoding CD154, with verification carried out via the restriction pattern of the restriction enzyme ScaI and sequencing. Said plasmid was referred to as pJF118ut-CD154-Pal (see FIG. 4 for the plasmid map).

Example 1: Production of Cyclodextrin Glycosyltransferase (CGTase) in a Shake Flask For the production of the CGTase from *Klebsiella pneumoniae* M5a1, the *E. coli* strain W3110 (ATCC 27325) was transformed with the plasmids pCGT, pCGT-Pal, pCGT-Pal22A or pCGT-TolAIII by common methods (e.g., TSS transformation). The selection for plasmid-containing cells was done by means of tetracycline (20 mg/l). The *E. coli* strains were designated W3110/pCGT, W3110/pCGT-Pal, W3110/pCGT-Pal22A and W3110/pCGT-TolAIII.

The transformed strains were grown at 30° C. in 10 ml of LB medium (5 g/l yeast extract (Oxoid LP0021), 10 g/l tryptone (Oxoid LP0042), 5 g/l NaCl), additionally containing 1 ml/l trace element solution (0.15 g/l $Na_2MoO_4 \times 2\ H_2O$; 2.5 g/l $Na_3BO_3$; 0.7 g/l $CoCl_2 \times 6\ H_2O$; 0.25 g/l $CuSO_4 \times 5\ H_2O$; 1.6 g/l $MnCl_2 \times 4\ H_2O$; 0.3 g/l $ZnSO_4 \times 7\ H_2O$), 3 g/l glucose, 10 g/l lactose, 0.55 g/l $CaCl_2$) and 20 mg/l tetracycline. The medium used was an autoinduction medium, i.e., it was not necessary to add additional inducer for the tac promoter. After metabolization of the glucose present in the medium, it was possible for the lactose to be taken up by the cells. This led to the induction of protein expression proceeding from the tac promoter. CGTase was produced by all four plasmids.

As a result of addition of 0.2% (w/v) arabinose after 48 h to the culture medium, there was additional induction by the plasmids pCGT-Pal and pCGT-Pal22A of the expression of the Pal variants which are also present on the plasmid and are under the control of the arabinose promoter and, by contrast, additional induction by the plasmid pCGT-TolAIII of the expression of TolAIII. The control cultures containing the plasmid pCGT were, too, appropriately admixed with arabinose for better comparability.

After a culture period of 72 h, samples were collected, the cells were removed from the culture medium by centrifugation, and the CGTase content in the culture supernatant was determined on the basis of the amount of cyclodextrin (CD) produced enzymatically from starch by means of the following enzyme assay:

Assay buffer: 5 mM Tris HCl buffer, 5 mM $CaCl_2 \times 2H_2O$, pH 6.5
Substrate solution: 10% starch solution (Merck No. 1.01252) in assay buffer, pH 6.5
Assay mix: 0.2 ml of substrate solution+0.2 ml of centrifuged (5 min, 12 000 rpm) culture supernatant
Reaction temperature: 40° C.
Enzyme Assay:
Preadjusting the temperature of substrate solution and centrifuged culture supernatant (approx. 5 min at 40° C.)
Preparing the assay mix by rapid mixing (whirl mixer) of substrate solution and centrifuged culture supernatant, the centrifuged culture supernatant being diluted with assay buffer if necessary so that a value of 0.9-1.5 g/l CD is determined in the subsequent HPLC analysis;
Incubating for 3 min at 40° C.
Stopping the enzyme reaction by addition of 0.6 ml of methanol and rapid mixing (whirl mixer)
Cooling the mix on ice (approx. 5 min)
Centrifuging (5 min, 12 000 rpm) and pipetting off the clear supernatant
Analyzing the amount of CD produced by means of HPLC: The analysis was carried out on an Agilent HP 1100 HPLC system with a Nucleodur 100-3 NH2-RP column (150 mm×4.6 mm, Macherey-Nagel) and 64% acetonitrile in water (v/v) as mobile phase, at a flow rate of 2.1 ml/min. Detection was achieved via an RI detector (1260 Infinity RI, Agilent) and quantification was performed on the basis of the peak area and an α-CD standard (Cavamax W6-8 Pharma, Wacker Chemie AG).

Calculation of enzyme activity: $A = G*V1*V2/(t*MG)$ [U/ml]
A=activity,
G=CD content in mg/l
V1=dilution factor in the assay mix
V2=dilution factor of the culture supernatant before use in the assay;
if undiluted, then: V2=1
t=reaction time in min
MG=molecular weight in g/mol ($MG_{CD}$=973 g/mol)
1 unit (U)≙1 µmol/l product (CD)/min
Table 1 shows the respectively achieved CGTase yields.

TABLE 1

| CGTase yields in the shake flask supernatant after 72 h of culturing. | |
|---|---|
| Strain | Shake flask: CGTase (U/ml) |
| W3110/pCGT | 39 |
| W3110/pCGT-Pal | 134 |
| W3110/pCGT-Pal22A | 95 |
| W3110/pCGT-TolAIII | 42 |

Example 2: Fermentative Production of Cyclodextrin Glycosyltransferase (CGTase) in a Stirred Tank Fermenter The strains described in Example 1, W3110/pCGT, W3110/pCGT-Pal and W3110/pCGT-TolAIII, were used for the production of the cyclodextrin glycosyltransferase (CGTase) from *Klebsiella pneumoniae* M5a1.

CGTase production was carried out in stirred tank fermenters. The fermenter filled with 1.2 l of the fermentation medium (1.5 g/l $KH_2PO_4$; 5 g/l $(NH_4)_2SO_4$; 0.5 g/l $MgSO_4 \times 7\ H_2O$; 0.225 g/l $CaCl_2) \times 2H_2O$, 0.075 g/l $FeSO_4 \times 7\ H_2O$; 1 g/l $Na_3$ citrate×$2H_2O$; 0.5 g/l NaCl; 1 ml/l trace element solution (0.15 g/l $Na_2MoO_4 \times 2\ H_2O$; 2.5 g/l $Na_3BO_3$; 0.7 g/l $CoCl_2 \times 6\ H_2O$; 0.25 g/l $CuSO_4 \times 5\ H_2O$; 1.6 g/l $MnCl_2 \times 4\ H_2O$; 0.3 g/l $ZnSO_4 \times 7\ H_2O$); 5 mg/l vitamin B1; 3 g/l phytone peptone (BD 211906); 1.5 g/l yeast extract (Oxoid LP0021); 10 g/l glucose; 20 mg/l tetracycline) was inoculated to 0.1 $OD_{600}$ with a preliminary culture which had been cultured in the LB medium mentioned under Example 1 in a shake flask for 7 h. The fermentation was thereby started (time point 0, start of fermentation). During the fermentation, a temperature of 30° C. was set and the pH was kept constant at a value of 7.0 by metering in $NH_4OH$ or $H_3PO_4$. Glucose was metered in over the fermentation, with a glucose concentration of <5 g/l being striven for. The expression of the CGTase was induced by addition of isopropyl β-D-thiogalactopyranoside (IPTG) to 0.15 mM after 22 h (at the end of the logarithmic growth phase). The expression of the Pal variant was induced 24 h or 41 h after the start of fermentation and the expression of TolAIII was induced 41 h after the start of fermentation by switching the pure glucose feed to a constant feed of glucose/arabinose mix of 3 g/l*h in the glucose:arabinose ratio of 2:1.

Before inoculation, the medium in the fermenter was stirred at 400 rpm and sparged with 1.67 vvm (volume of air per volume of culture medium per minute) of compressed air sterilized via a sterile filter. Under these starting conditions, the optical oxygen sensor (VisiFerm DO225, Hamilton) was calibrated to 100% saturation before the inoculation. The target value for the 02 saturation during the fermentation was set to 30% of this value. The $O_2$ saturation was measured via the oxygen sensor during the fermentation and captured by the fermenter control DCU (digital control unit, Sartorius Stedim). After the O2 saturation fell below the target value, the stirring speed was increased continuously under software control to a maximum of 1500 rpm in order to bring the $O_2$ saturation back to the target value.

After 48 h of fermentation, samples were collected, the cells were removed from the fermentation medium by centrifugation, and the CGTase content in the fermentation supernatant was determined by the activity assay as described in Example 1. Table 2 shows the respectively achieved cyclodextrin glycosyltransferase yields.

TABLE 2

CGTase yields in the fermentation supernatant after 48 h of culturing.

| Strain | CGTase (relative yield in %) |
|---|---|
| W3110/pCGT | 100 |
| W3110/pCGT-Pal, induction after 24 h | 430 |
| W3110/pCGT-Pal, induction after 41 h | 690 |
| W3110/pCGT-TolAIII | 260 |

The influence of the expression of the Pal variant on cell growth was investigated by determining, in the course of fermentation for W3110/pCGT and W3110/pCGT-Pal (induction after 41 h), the growth of the cells via measurement of optical density at 600 nm ($OD_{600}$) on a spectrophotometer (Beckman Coulter DU 730).

In addition, the cell dry weight of the cultures was determined. To determine the cell dry weight, samples containing 1 ml of fermenter culture were transferred into reaction vessels, the empty weight of which had been determined beforehand. After centrifugation (5 min, 12 000 rpm), the supernatants were removed and the cell pellets were dried in an incubator (≥48 h at 60° C.). Thereafter, the vessels containing the dried cell pellet were weighed out and the cell dry weight (CDW) was calculated from the difference between the weight of the vessels containing dried cell pellet and the weight of the empty vessels. The results are combined in Table 3.

TABLE 3

Optical density ($OD_{600}$) and cell dry weight (CDW) of the CGTase-producing strains in the fermenter.

| | $OD_{600}$ Culture period | | CDW (g/l) Culture period | |
|---|---|---|---|---|
| Strain | 41 h | 48 h | 41 h | 48 h |
| W3110/pCGT | 142 | 153 | 51 | 55 |
| W3110/pCGT-Pal, induction after 41 h | 146 | 150 | 52 | 52 |

Example 3: Production of a Fab Antibody Fragment in a Shake Flask

The production of the CD154 Fab fragment in a shake flask was carried out analogously to the method described in Example 1 using the *E. coli* strains W3110/pJF118ut-CD154 and W3110/pJF118ut-CD154-Pal. After 72 h, samples were collected, the cells were removed from the culture medium by centrifugation, and the supernatant was analyzed to determine the CD154 Fab fragment released into the culture medium. The cell pellet was gathered in PBS buffer and the cells were disrupted on a FastPrep homogenizer (MP Biomedicals). The CD154 Fab fragment present intracellularly was determined from the cell lysate thus obtained.

The CD154 Fab fragment was quantified via a sandwich ELISA assay known to a person skilled in the art. This involved using an immobilized anti-human IgG (Fd) antibody (The Binding Site, product No. PC075) as catcher and a peroxidase-conjugated goat anti-human kappa light chains antibody (Sigma, product no. A 7164) as detection antibody. Quantification was achieved by conversion of the chromogenic substrate Dako TMB+ (Dako #S1599) by the peroxidase and the associated absorption change at 450 nm. The ELISA was calibrated using the Fab fragment "Human Fab/Kappa" (Bethyl Laboratories, product number: P80-115).

TABLE 3

Yields of CD154 antibody fragment in the culture supernatant.

| Strain | CD154 antibody fragment (mg/l) in the supernatant |
|---|---|
| W3110/pJF118ut-CD154 | 59 |
| W3110/pJF118ut-CD154-Pal | 87 |

In addition to the product yield, the live cell count of the cultures was also determined after 72 h. To this end, samples of the cultures were diluted $10^5$-fold with LB medium in a final volume of 1 ml, and 100 µl of the dilution were plated out in each case on LB agar plates containing 20 mg/l tetracycline. The colonies grown were counted, and the live cell count of the starting cultures was calculated taking into account the dilution factor. This was $5.5 \cdot 10^8$ cells/ml for the strain W3110/pJF118ut-CD154 and $2.7 \cdot 10^8$ cells/ml for the strain W3110/pJF118ut-CD154-Pal.

The invention claimed is:

1. A bacterial strain for producing and releasing a recombinant protein, the bacterial strain containing an open reading frame encoding the recombinant protein under the control of a functional promoter,
wherein the bacterial strain contains an open reading frame encoding a mutated peptidoglycan-associated lipoprotein (Pal protein) under the control of a functional promoter, the mutated Pal protein having been mutated such that it has no membrane anchor for the outer cell membrane of the bacterium,
the 5' end of the coding DNA sequence of both proteins to be produced being linked in frame with the 3' end of a signal sequence for protein export so that both the recombinant protein and the mutated Pal protein are transported into the periplasm after protein biosynthesis in the cytosol,
the bacterial strain additionally containing a wild-type Pal gene and
the bacterial strain being Gram-negative.

2. The bacterial strain of claim 1, wherein the bacterial strain is a strain of the species *Escherichia coli*.

3. The bacterial strain of claim 1, wherein the open reading frame encoding the mutated Pal protein has been mutated such that it encodes a mutated Pal protein which has been mutated at one or more of amino acid positions 1 to 6.

4. The bacterial strain as claimed in claim 3, wherein the open reading frame encoding the mutated Pal protein has been mutated such that it encodes a mutated Pal protein in which the N-terminal cysteine residue has been substituted.

5. The bacterial strain of claim 3, wherein the open reading frame encoding the mutated Pal protein has been mutated such that it encodes a mutated Pal protein in which the N-terminal cysteine residue is absent.

6. The bacterial strain of claim 3, wherein the open reading frame encoding the mutated Pal protein has been mutated such that it encodes a mutated Pal protein in which amino acids 1 to 6 are absent.

7. The bacterial strain of claim 1, wherein the recombinant protein is a heterologous protein.

8. A method for fermentative production of recombinant proteins, comprising: culturing a bacterial strain, in a fermentation medium, removing the fermentation medium from cells of the bacterial strain, and isolating recombinant proteins from the fermentation medium, wherein the bacterial strain contains an open reading frame encoding a mutated peptidoglycan-associated lipoprotein (Pal protein) under the control of a functional promoter, the mutated Pal protein having been mutated such that it has no membrane anchor for the outer cell membrane of the bacterium,
the 5' end of the coding DNA sequence of both proteins to be produced being linked in frame with the 3' end of a signal sequence for protein export so that both the recombinant protein and the mutated Pal protein are transported into the periplasm after protein biosynthesis in the cytosol,
the bacterial strain additionally containing a wild-type Pal gene and
the bacterial strain being Gram-negative.

9. The method of claim 8, wherein the recombinant proteins are purified from the fermentation medium after the removal of the fermentation medium.

10. The method of claim 8, wherein that expression of the mutated Pal protein is induced.

11. The method of claim 8, wherein expression of the mutated Pal protein is induced after induction of expression of the recombinant protein.

12. The method of claim 8, wherein the open reading frame encoding the mutated Pal protein has been mutated such that it encodes a mutated Pal protein in which the N-terminal cysteine residue is absent.

13. The method of claim 8, wherein the open reading frame encoding the mutated Pal protein has been mutated such that it encodes a mutated Pal protein in which amino acids 1 to 6 are absent.

* * * * *